US011587647B2

United States Patent
Hao et al.

(10) Patent No.: US 11,587,647 B2
(45) Date of Patent: Feb. 21, 2023

(54) PROCESSING PROFILES USING MACHINE LEARNING TO EVALUATE CANDIDATES

(71) Applicant: International Business Machines Corporation, Armonk, NY (US)

(72) Inventors: Bibo Hao, Beijing (CN); Shouyu Yan, Beijing (CN); Eryu Xia, Beijing (CN); Shi Lei Zhang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 196 days.

(21) Appl. No.: 16/542,938

(22) Filed: Aug. 16, 2019

(65) Prior Publication Data

US 2021/0050075 A1 Feb. 18, 2021

(51) Int. Cl.
*G16H 10/20* (2018.01)
*G16H 50/30* (2018.01)
*G16H 50/20* (2018.01)
*G16H 10/60* (2018.01)

(52) U.S. Cl.
CPC ............. *G16H 10/20* (2018.01); *G16H 10/60* (2018.01); *G16H 50/20* (2018.01); *G16H 50/30* (2018.01)

(58) Field of Classification Search
CPC ........ G16H 10/20; G16H 50/30; G16H 50/20; G16H 10/60
See application file for complete search history.

(56) References Cited

U.S. PATENT DOCUMENTS

| 9,767,526 | B2 | 9/2017 | Martinez et al. |
| 2002/0099570 | A1 | 7/2002 | Knight |
| 2003/0086612 | A1* | 5/2003 | Hullender ............ G06K 9/6293 382/187 |
| 2005/0210015 | A1 | 9/2005 | Zhou et al. |
| 2006/0173663 | A1* | 8/2006 | Langheier ............. G16H 50/50 703/11 |
| 2014/0316793 | A1 | 10/2014 | Pruit |
| 2015/0088541 | A1* | 3/2015 | Yao ....................... G16H 20/00 705/2 |
| 2016/0246945 | A1* | 8/2016 | Allen ..................... G16H 50/20 |
| 2017/0061102 | A1* | 3/2017 | Weber .................... G06F 19/00 |
| 2018/0046780 | A1* | 2/2018 | Graiver ................. G16H 10/60 |
| 2018/0151253 | A1 | 5/2018 | Neal |
| 2018/0341255 | A1* | 11/2018 | Turney ............... G05B 23/0294 |
| 2020/0211715 | A1* | 7/2020 | Walter ............... G06Q 10/1053 |

OTHER PUBLICATIONS

Emero, "AI and Machine Learning for Clinical Trials—Examining 3 Current Applications," 15 pages, Jan. 28, 2019.

(Continued)

*Primary Examiner* — Gregory D. Moseley
(74) *Attorney, Agent, or Firm* — Patterson + Sheridan, LLP (57) ABSTRACT

Techniques for candidate evaluation and filtering are provided. Enrollment criteria for a clinical trial are received, where the enrollment criteria include a plurality of conditions. A plurality of cost vectors is constructed for the plurality of conditions. A set of values for one or more of the plurality of conditions is determined for a candidate, where the set of values does not include a value for at least a first condition of the plurality of conditions. A utilized cost is generated for the candidate, based on the first set of values and the plurality of cost vectors. The candidate is then ranked based on the utilized cost.

14 Claims, 8 Drawing Sheets

(56) References Cited

OTHER PUBLICATIONS

Maxine Bookbinder, "The Intelligent Trial: AI Comes to Clinical Trials," Mar. 14-15, 2019, 4 pages.
S.T. Frantz, Why are clinical costs so high? Nature Reviews Drug Discovery. 2 (2003) 851-851. doi:10.1038/nrd1250. [Abstract Only].
A.M. McDonald, R.C. Knight, M.K. Campbell, V.A. Entwistle, A.M. Grant, J.A. Cook, D.R. Elbourne, D. Francis, J. Garcia, I. Roberts, and C. Snowdon, What influences recruitment to randomized controlled trials? A review of trials funded by two UK funding agencies, Trials. 7 (2006). doi: 10.1186/1745-6215-7-9.
C. Patel, J. Cimino, J. Dolby, A. Fokoue, A. Kaiyanpur, A. Kershenbaum, L. Ma, E. Schonberg, and K. Srinivas, Matching Patient Records to Clinical Trials Using Ontologies, in: K. Aberer, K.-S. Choi, N. Noy, D. Allemang, K.-I. Lee, L, Nixon, J. Golbeck, P. Mika, D. Maynard, R. Mizoguchi, G. Schreiber, and P. Cudre-Mauroux (Eds.), The Semantic Web, Springer Berlin Heidelberg, Berlin, Heidelberg, 2007: pp. 816-829. doi:10.1007/978-3-540-76298-0_59.
J.S. Breese, D. Heckerman, and C. Kadie, Empirical Analysis of Predictive Algorithms for Collaborative Filtering, ArXiv:1301.7363 [Cs], (2013). http://arxiv.org/abs/1301.7363 (accessed Nov. 25, 2018).
G.H. Golub, and C. Reinsch, Singular value decomposition and least squares solutions, Numerische Mathematik. 14 (1970) 403-420. doi: 0.1007/BF02163027. [Abstract Only].
J. Walonoski, M. Kramer, J. Nichois, A. Quina, C. Moesel, D. Hall, C. Duffett, K. Dube, T. Gallagher, and S. McLachlan, Synthea: An approach, method, and software mechanism for generating synthetic patients and the synthetic electronic health care record, Journal of the American Medical Informatics Association. 25 (2018) 230-238. doi: 10.1093/jamia/ocx079.

\* cited by examiner

| PATIENT | CONDITION 1 | CONDITION 2 | CONDITION 3 | CONDITION 4 | ... | CONDITION N |
|---|---|---|---|---|---|---|
| P1 | 24.1 | 0 | 0 | | ... | 0 |
| P2 | 50.0 | | | 2.49 | ... | 0 |
| P3 | 120.3 | | | 1.81 | ... | |
| P4 | | | | 30.2 | ... | |
| ... | | | | | ... | |
| Pm | 60.0 | | | 2.75 | ... | |

↓ BINARY CONVERSION 225

230

| PATIENT | CONDITION 1 | CONDITION 2 | CONDITION 3 | CONDITION 4 | ... | CONDITION N |
|---|---|---|---|---|---|---|
| P1 | 1 | 0 | 0 | | ... | 0 |
| P2 | 1 | | | 1 | ... | 0 |
| P3 | 0 | | | 1 | ... | |
| P4 | | | | 1 | ... | |
| ... | | | | | ... | |
| Pm | 1 | | | 0 | ... | |

↓ SPARSITY REDUCTION 235

240

| PATIENT | CONDITION 1 | CONDITION 2 | CONDITION 3 | CONDITION 4 | ... | CONDITION N |
|---|---|---|---|---|---|---|
| P1 | 1 | 0 | 0 | | ... | 0 |
| P2 | 1 | 0.54 | | 1 | ... | 0 |
| P3 | 0 | 0.92 | | 1 | ... | 0.89 |
| P4 | 0.82 | | | 0.14 | ... | |
| ... | | | | | ... | |
| Pm | 1 | 1 | 0.55 | 0 | ... | |

PROCESSING PROFILES USING MACHINE LEARNING TO EVALUATE CANDIDATES

BACKGROUND

The present disclosure relates to machine learning, and more specifically, to using machine learning in order to efficiently identify candidate patients.

Clinical trials are an important process for researchers to develop new treatments, as well as evaluate their effectiveness and safety. However, more than half of all clinical trials experience delays, leading to a considerable increase in cost. In typical clinical trials, human participants are recruited for experiments or observations. The number of participants required can vary from tens to thousands, depending on the phase and research purpose. Unfortunately, clinical trial recruitment is often slower and more difficult than expected, and many trials fail to reach their planned sample size within the timescale and funding originally envisaged. Such delay or failure of clinical trials leads to considerable waste of money and time, and also represents significant lost opportunity cost.

SUMMARY

According to one embodiment of the present disclosure, a method is provided. The method includes receiving enrollment criteria for a clinical trial, wherein the enrollment criteria include a plurality of conditions. The method further includes constructing a plurality of cost vectors for the plurality of conditions. Additionally, the method includes determining, for a first patient, a first set of values for one or more of the plurality of conditions, wherein the first set of values does not include a value for at least a first condition of the plurality of conditions. A first utilized cost is generated for the first patient, based on the first set of values and the plurality of cost vectors. The method also includes ranking the first patient based on the first utilized cost.

According to a second embodiment of the present disclosure, a computer-readable storage medium is provided. The computer-readable storage medium contains computer program code that, when executed by operation of one or more computer processors, performs an operation. The operation includes receiving enrollment criteria for a clinical trial, wherein the enrollment criteria include a plurality of conditions. The operation further includes constructing a plurality of cost vectors for the plurality of conditions. Additionally, the operation includes determining, for a first patient, a first set of values for one or more of the plurality of conditions, wherein the first set of values does not include a value for at least a first condition of the plurality of conditions. A first utilized cost is generated for the first patient, based on the first set of values and the plurality of cost vectors. The operation also includes ranking the first patient based on the first utilized cost.

According to a third embodiment of the present disclosure, a system is provided. The system includes one or more computer processors, and a memory containing a program which, when executed by the one or more computer processors, performs an operation. The operation includes receiving enrollment criteria for a clinical trial, wherein the enrollment criteria include a plurality of conditions. The operation further includes constructing a plurality of cost vectors for the plurality of conditions. Additionally, the operation includes determining, for a first patient, a first set of values for one or more of the plurality of conditions, wherein the first set of values does not include a value for at least a first condition of the plurality of conditions. A first utilized cost is generated for the first patient, based on the first set of values and the plurality of cost vectors. The operation also includes ranking the first patient based on the first utilized cost.

DETAILED DESCRIPTION

Embodiments of the present disclosure provide a cost-effective framework for data evaluation and analysis in a way that facilitates recruiting and screening eligible clinical trial participants. By leveraging the observed conditions of patients, as well as the cost of medical examinations, embodiments of the present disclosure utilize collaborative filtering techniques to predict the utilized cost for any needed medical examinations. In some embodiments, patients and medical examinations can be ranked based on their utilized costs.

Typical challenges faced during clinical trial recruitment include fewer eligible patients than expected, fewer patients agreeing to participate than expected, many eligible patients missed, and the like. In embodiments, electronic medical records (EMRs) can facilitate identification of eligible patients. In some embodiments, artificial intelligence technologies like natural language processing (NLP) are applied to understand patient medical records, in order to accelerate clinical trial recruiting process. However, in many cases, important condition values for the various patients are not available in EMRs. Often, these values are missing because the patient has not undergone some medical examination, or the results of the examination(s) are not recorded in the EMR system.

If a given clinical trial criterion specifies acceptable values for these conditions, however, it is impossible determine the eligibility of the patients with unobserved values for the conditions. In many embodiments, the patient must undergo medical examination(s) in order to determine values for these unobserved conditions, in order to determine eligibility. The costs of conducting these medical examinations are often paid by patients, and/or from the limited clinical trial budget. Frequently, however, patients who agree to undergo these additional examinations are found to be ineligible for the trial, as the unobserved conditions may fail to satisfy the required criteria.

Given patient data with missing values (also referred to as unobserved conditions), embodiments of the present disclosure provide techniques to evaluate and analyze the underlying data in order to maximize the probability of selecting patients who will meet the eligibility criteria, while minimizing the cost of medical examinations. In some embodiments, in addition to which patients that should be selected and evaluated first, systems described herein provide techniques to evaluate and rank medical examinations for a given patient, in order to determine the order in which tests should be performed. This can dramatically reduce costs in evaluating patient data. In various embodiments, these costs can include monetary cost, time expenditures, and the like. In some embodiments, the cost analysis further includes consideration of the invasiveness of the procedure, in order to reduce the burden on the patient.

In one embodiment, "utilized cost" refers to the expected or predicted cost of ensuring that a patient satisfies one or more predefined criteria. In embodiments, the utilized cost is based on the probability that the patient's condition satisfies the criteria, along with the costs that will be incurred to confirm that the patient satisfies the criteria. For example, if it is already known that a first patient satisfies a first criterion, the first patient's utilized cost with respect to the first criterion is zero (e.g., nothing need be expended to confirm that the patient is eligible). Similarly, if it is known that a second patient does not satisfy the first criterion, the second patient's utilized cost with respect to the first criterion is infinite (e.g., no amount of expenditure can confirm that the patient eligible). In an embodiment, the probability of satisfying the criteria is inversely correlated with the utilized cost (such that higher probabilities correlate with lower utilized costs). Further, in embodiments, the cost of the needed medical examination(s) is directly correlated with the utilized cost (such that higher costs of examination correlate with higher utilized costs).

Figure 1:
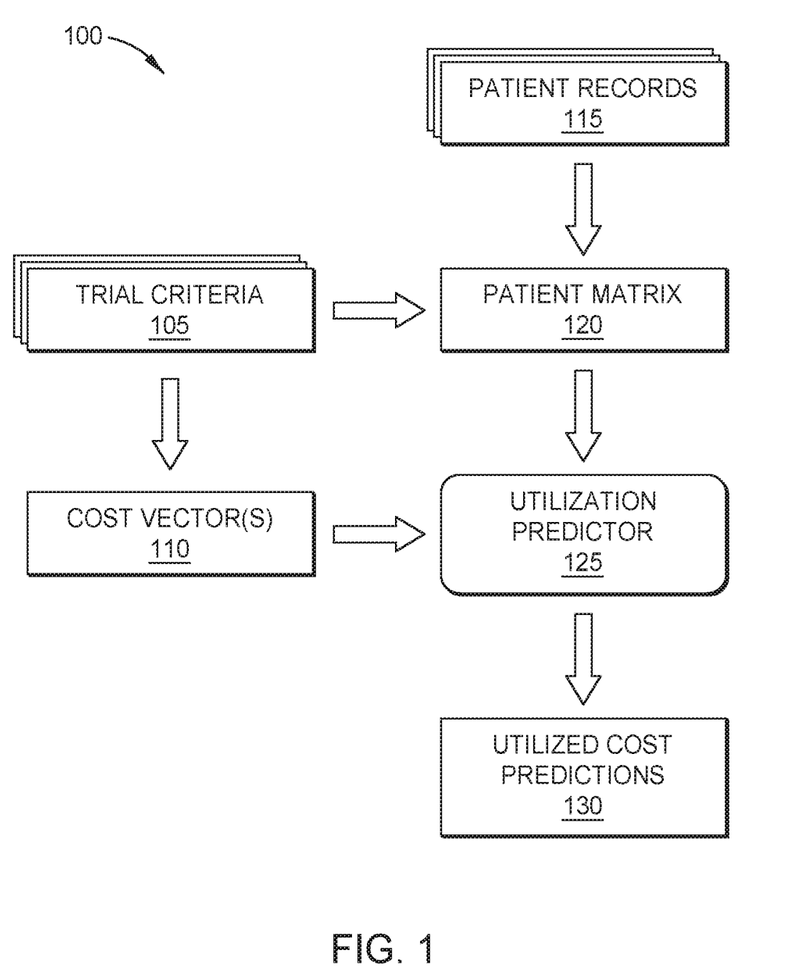
FIG. 1 illustrates a workflow for evaluating patient records and trial data to predict utilized costs, according to one embodiment disclosed herein.

FIG. 1 illustrates a workflow 100 for evaluating patient records and trial data to predict utilized costs, according to one embodiment disclosed herein. In the illustrated workflow 100, a set of Patient Records 115 and Trial Criteria 105 are received and evaluated in order to generate a Patient Matrix 120. In the illustrated embodiment, the Patient Records 115 correspond to any patient data, such as EMRs, survey responses, and the like. Generally, each Patient Record 115 specifies one or more values or conditions of the corresponding patient(s). As used herein, a condition can include any characteristic, status, or parameter of the patient, and can include textual values, binary values (e.g., whether or not the patient has a given disorder), as well as numerical values. In various embodiments, the conditions can include any medical characteristic, such as the patient's age, blood sugar level, blood pressure, cancer status, and the like. In some embodiments, the Patient Records 115 include natural language text, and one or more NLP techniques are used to extract the relevant condition values.

In the illustrated embodiment, the Trial Criteria 105 are specified requirements for one or more clinical trials. In one embodiment, each criterion specifies a condition (e.g., age), as well as corresponding acceptable value(s) and/or range(s) of values (e.g., greater than or equal to sixty). In an embodiment, the Patient Matrix 120 is constructed based on the Trial Criteria 105 and Patient Records 115. In one embodiment, each row in the Patient Matrix 120 corresponds to a patient from the Patient Records 115, while each column corresponds to a condition specified in the Trial Criteria 105. In such an embodiment, the intersection of a given row and column indicates the value of the corresponding condition, with respect to the corresponding patient. In embodiments, if the value for a condition is unknown with respect to a particular patient (e.g., it is not found or cannot be understood or interpreted in the Patient Records 115), the corresponding cell in the Patient Matrix 120 is left blank or is otherwise marked as "unknown."

In some embodiments, the Patient Matrix 120 may include one or more additional columns for conditions that are not implicated by the Trial Criteria 105. For example, in such an embodiment, the Patient Matrix 120 may include a column for "age," even if the Trial Criteria 105 do not specify any required age. In such an embodiment, these additional conditions may be useful in generating predicted values for missing data, as discussed below in more detail.

As illustrated, the Trial Criteria 105 are additionally used to generate one or more Cost Vectors 110. In an embodiment, each Cost Vector 110 indicates the cost of determining a patient value for a corresponding condition that is specified in the Trial Criteria 105. That is, in such an embodiment, for each condition specified in the Trial Criteria 105, the system defines a corresponding Cost Vector 110. For example, a first Cost Vector 110 may indicate a cost of determining the patient's age, while a second Cost Vector 110 indicates the cost of determining the patient's insulin levels. In some embodiments, the Cost Vectors 110 can include a variety of dimensions, such as monetary cost, time cost, invasiveness of the required tests, and the like. In one embodiment, if the Cost Vectors 110 are multi-dimensional, a single cost value can be defined as an aggregate cost across all dimensions, for each condition.

In the illustrated embodiment, the Cost Vectors 110 and Patient Matrix 120 are provided to a Utilization Predictor 125, which evaluates them to generate one or more Utilized Cost Predictions 130. In one embodiment, this evaluation includes generating a predicted value for each unknown value in the Patient Matrix 120. In some embodiments, this prediction includes applying one or more machine learning techniques to predict patient values. In various embodiments, for example, predicting patient values can involve identifying similar patients (with known values for a given condition) to compare each patient to, utilizing one or more Collaborative Filtering (CF) techniques to reduce the sparsity of the matrix and/or to predict missing values, such as matrix factorization (e.g., singular value decomposition (SVD)), user-based similarity models (UBSMs), restricted Boltzmann machines (RBMs), and/or latent factor models (LFMs) to predict missing values, and the like.

In an embodiment, once the predicted values are determined, the Utilization Predictor 125 evaluates the Cost Vectors 110 to determine, for each patient, an overall utilized cost. In this way, the patients can be ranked or sorted based on their overall utilized costs. By iteratively selecting patients with low utilized costs, the overall expenditure needed to identify a sufficient number of eligible patients can be dramatically reduced. Further, in some embodiments, the Utilization Predictor 125 similarly generates a utilized cost for each condition. In such an embodiment, once a patient is selected for evaluation, the needed tests or examinations can be indicated and sorted or ranked based on their individual utilized costs. This can similarly reduce the expenditure required to confirm or reject each individual patient.

Figure 2A:
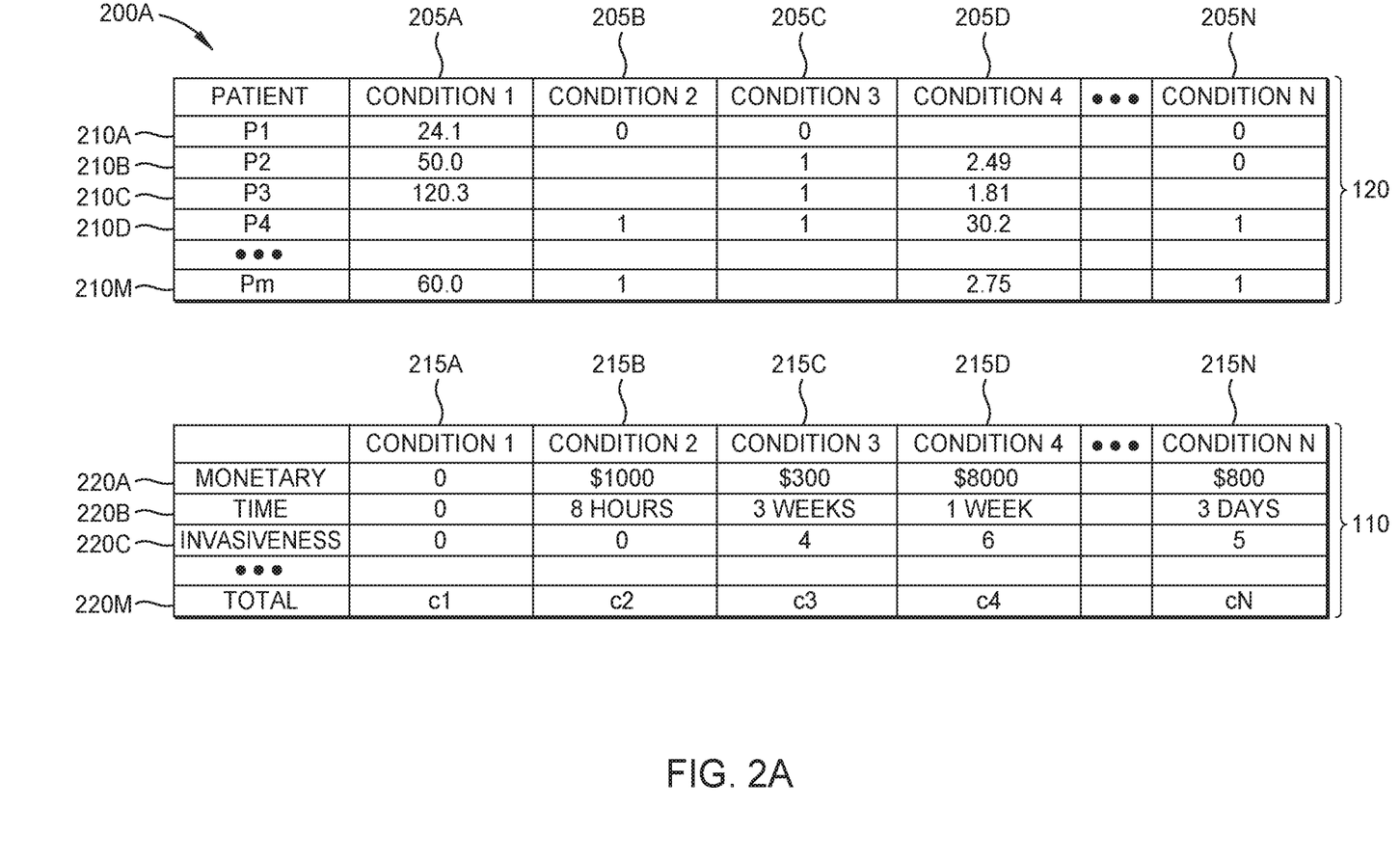
FIGS. 2A-2C depict a workflow for generating utilized cost predictions based on patient data, according to one embodiment disclosed herein.
Figure 2B:
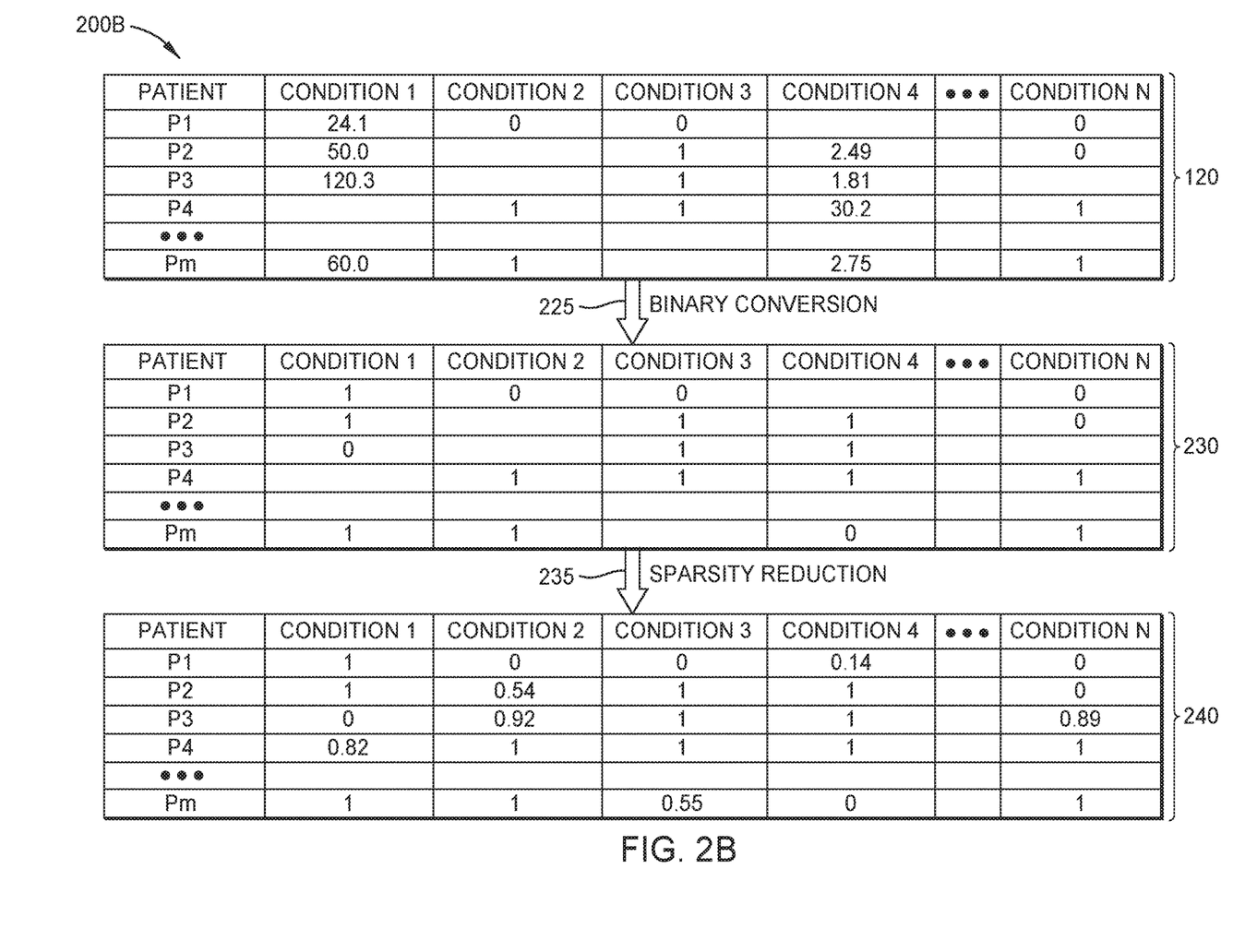
Figure 2C:
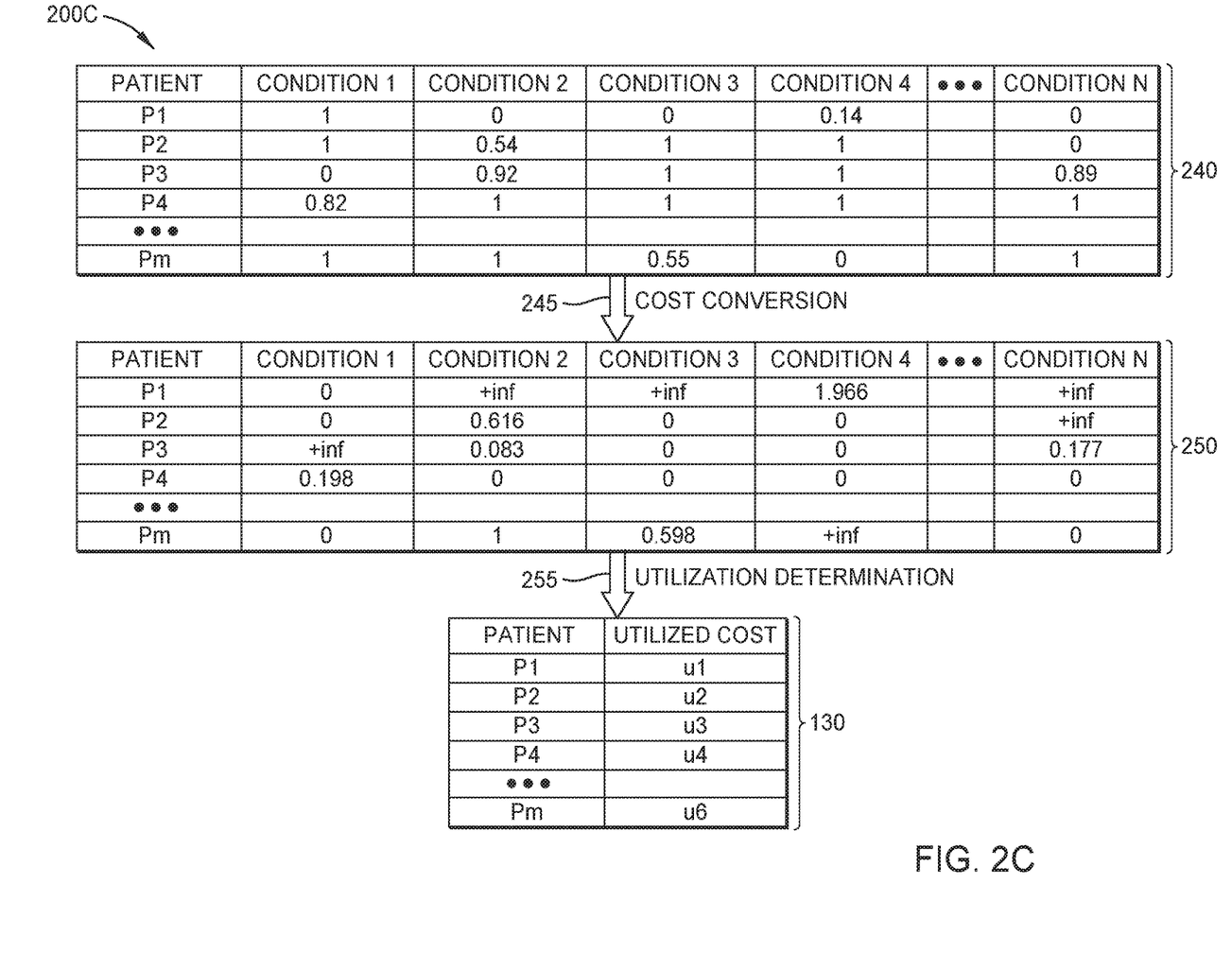

FIGS. 2A-2C depict a workflow for generating utilized cost predictions based on patient data, according to one embodiment disclosed herein. As illustrated in FIG. 2A, the workflow begins at a first stage 200A, where the Patient Matrix 120 and Cost Vectors 110 are constructed. In the illustrated embodiment, the Patient Matrix 120 includes a row 210A-M for each patient, as well as a column 205A-N for each condition. Further, each cell or field in the Patient Matrix 120 includes a value for the corresponding patient, with respect to the corresponding condition. For example, the patient "P3" has a value of "1.81" for the condition "Condition4" (indicated by the intersection between row 210C and column 205D). In an embodiment, the Patient Matrix 120 is constructed using the Patient Records 115. For example, the values may be extracted from natural language text in the records using one or more NLP techniques, or may otherwise be specified in EMRs.

In the illustrated embodiment, empty or blank sections of the Patient Matrix 120 indicate that the value of the corresponding condition for the corresponding patient is unknown or cannot be determined. This may indicate that the patient has not undergone one or more examinations or tests needed to provide a value, has not responded to a survey or questionnaire that would provide a value, and the like. For example, as illustrated, the patient "P3" has no known value for "Condition2" or "ConditionN." In some embodiments, the patients represented in the Patient Matrix 120 have been pre-selected as potentially eligible and/or interested participants for the study (e.g., by one or more medical providers or based on their condition values). In another embodiment, the Patient Matrix 120 includes all potentially-available patients (e.g., within a defined geographic area, or all patients for whom data is available).

As illustrated, the set of Cost Vectors 110 include a column or vector 215A-N for each condition, where each row 220A-E corresponds to a type of cost. For example, in the illustrated embodiment, the column 215A corresponds to one or more tests, examinations, surveys, procedures, and the like that are used to determine a value for the condition "Condition1." As illustrated, each cost vector indicates a monetary cost to determine a value for the corresponding condition, a time required until the value is known, and an invasiveness of the test(s). For example, the Condition1 has a monetary cost, time cost, and invasiveness of zero. That is, the cost of determining a value for Condition1 costs no (or very little) money, takes no (or almost no) time, and is minimally invasive. For example, Condition1 may correspond to the patient's age or sex. In contrast, determining a value for Condition4 will cost about $8000, will take about a week to get results, and is rated as a "six" on the invasiveness scale. In an embodiment, the invasiveness cost uses a predefined scale (e.g., based on whether the test involves questioning, puncture such as to draw blood, biopsy, DNA sequencing, endoscopy, and the like).

In one embodiment, the values in the Cost Vectors 110 are determined based on predefined costs associated with each test. In some embodiments, these are specified by a user (e.g., a medical professional conducting the study). In other embodiments, they can be determined by evaluating and analyzing medical literature. For example, in one embodiment, for each criterion specified in the Trial Criteria 105, a user can identify one or more corresponding tests that will be used to determine whether a given patient satisfies the criterion. The user can then specify a monetary cost, time cost, and/or invasiveness of the tests. In another embodiment, the system can evaluate medical literature to automatically identify potential tests for each condition, as well as the corresponding costs involved.

Additionally, in the illustrated embodiment, the Cost Vectors 110 include a total cost for each condition. In an embodiment, the total cost indicates an aggregate value to represent the overall cost of the test(s). In some embodiments, the total cost is a numerical value. In one embodiment, the user can specify weights for each dimension, in order to skew the resulting total costs based on the factors that are most important to the user and/or trial. For example, time may be an extremely important factor, while monetary cost is not as important. Similarly, for a different study, the budget may be limited (indicating that monetary cost should be weighted highly), while the time costs are not important (e.g., because the disorder being studied is stable and long-lasting).

As depicted in FIG. 2B, once the Patient Matrix 120 and Cost Vectors 110 are defined, the workflow moves to a second stage 200B where the Utilization Predictor 125 begins evaluating and analyzing the data. In the illustrated workflow, the Utilization Predictor 125 performs a Binary Conversion 225 on the Patient Matrix 120 in order to generate a Binary Matrix 230. In one embodiment, the Binary Conversion 225 is performed based on the Trial Criteria 105. That is, in an embodiment, the Utilization Predictor 125 determines whether to convert a given value to "zero" or "one" based on whether the value satisfies the corresponding criterion. In some embodiments, the Trial Criteria 105 can include inclusive criteria (i.e., criteria which, if satisfied, indicate that the patient is eligible) as well as exclusive criteria (i.e., criteria which, if satisfied, indicate that the patient is ineligible).

In embodiments, a value of "one" in the Binary Matrix 230 indicates that the patient is eligible for the study with respect to the corresponding condition/criterion, while a value of "zero" indicates that the patient is ineligible, with respect to the corresponding condition/criterion. For example, as illustrated, the patients "P1," "P2," and "P4" are eligible, with respect to Condition1, while the patient "P3" is ineligible based on Condition1. In some embodiments, if a patient is ineligible with respect to any conditions, they are ineligible for the study. In other embodiments, the patient may remain (potentially) eligible based on one or more other criteria, as specified in the Trial Criteria 105.

In one embodiment, if the Utilization Predictor 125 determines that a patient is conclusively ineligible for the study (e.g., because the patient has a value of "zero" for one or more fields in the Binary Matrix 230), the Utilization Predictor 125 removes this patient from further consideration. In other embodiments, the patient remains in the Binary Matrix 230 during further processing.

As illustrated, the Patient Matrix 120 and Binary Matrix 230 are both sparse. That is, they both have missing values. In the illustrated embodiment, the Utilization Predictor 125 performs Sparsity Reduction 235 in order to generate a value for each unknown field. In an embodiment, the Sparsity Reduction 235 comprises predicting whether the corresponding patient will satisfy the relevant criterion. For example, in the illustrated embodiment, the Utilization Predictor 125 has generated a value of 0.82 for P4, with respect to Condition1. That is, the Utilization Predictor 125 has predicted that there is an 82% change P4's value for Conditionl will satisfy the Trial Criteria 105.

In some embodiments, the Utilization Predictor 125 uses machine learning (ML) to predict a value for the unknown values, and/or to predict whether the unknown values will satisfy the criteria, when they are conclusively determined. For example, in one embodiment, the Utilization Predictor 125 uses a model trained to receive one or more patient attributes (e.g., known values in the matrix) and output predicted values for missing attributes. In another embodiment, for an index patient with one or more unknown attributes, the Utilization Predictor 125 identifies one or more similar patients based on the known attributes for the index patient, and infers or predicts values for the unknown attributes based on the actual values of the identified similar patients.

In some embodiments, the Utilization Predictor 125 utilizes collaborative filtering techniques, such as matrix factorization or a UBSM, to generate the missing values. In one such embodiment, a user-based similarity model (UBSM) is applied. In such an embodiment, given a patient $P_i$, the probability of this patient satisfying an eligibility criterion $C_j$ is defined using Equation 1:

$$q_{i,j} = \frac{\sum_{k \in P} simil(p_i, p_k) q_{k,j}}{\sum_{k \in P} |simil(p_i, p_k)|}$$

Equation 1

In Equation 1, P is the set of top N similar patient candidates' index, and simil(·) is a function used to calculate the similarity between the condition vectors of two patients. In one embodiment, the Pearson Correlation Coefficient is used as the similarity function. In other embodiments, other similarity functions can include vector cosine distance, and the like. In an embodiment, the UBSM is used to approximate the unobserved values by calculating the weighted average of top N similar patients.

In another embodiment, the Sparsity Reduction 235 includes using a Latent Factor Model (LFM). In such an embodiment, dimensionality reduction methods are used to compress the Binary Matrix 230 into a low-dimensional representation in terms of latent factors, which assumes that patients' conditions are the reflection of some low-dimensional latent factors. In one embodiment, the Singular Value Decomposition (SVD) algorithm is used to approximate patients' probabilities of satisfying eligibility criteria. The SVD algorithm factorizes the original patient-condition matrix into the dot product of three matrices: $V = P \Sigma C^T$, where P is an m×m unitary matrix representing the relationship of patient candidates, $\Sigma$ is an m×n diagonal matrix of singular values representing weights, and $C^T$ is an n×n unitary matrix representing the relationship of the condition values.

In embodiments, although the eligibility criteria for a given clinical trial cover only specified conditions (often ranging from five to fifty conditions with relevant criteria), a wide range of conditions (including ones not relevant to the specified Trial Criteria 105) are often recorded in the EMRs. In some embodiments, the Utilization Predictor 125 utilizes this additional information when predicting the probabilities.

In the illustrated embodiment, the Utilization Predictor 125 generates a Predictive Matrix 240 that includes the above-discussed binary values for known patient conditions (based on whether the value satisfies the Trial Criteria 105) as well as predictions regarding whether the unknown patient values will satisfy their corresponding criteria. In some embodiments, the Predictive Matrix 240 can be used to select and/or sort the patients. For example, the Utilization Predictor 125 can determine which patients are likely to satisfy the criteria (e.g., above a predefined threshold) based on the Predictive Matrix 240. Notably, however, the Predictive Matrix 240 does not include consideration of the costs that would be incurred to examine each patient in order to conclusively determine whether the patient is eligible. Thus, in an embodiment, simply selecting the patients with high probabilities may nevertheless result in wasted resources (e.g., if the required testing would be prohibitively expensive). Thus, in an embodiment, the Utilization Predictor 125 continues to analyze the data prior to generating recommendations.

As depicted in FIG. 2C, the processing moves to a third stage 200C, where the Utilization Predictor 125 performs Cost Conversion 245 on the Predictive Matrix 240 to generate a Converted Matrix 250. In an embodiment, the Cost Conversion 245 comprises calculating the negative natural log of each value in the Predictive Matrix 240. That is, for a given value $V_i$ in the Predictive Matrix 250, the corresponding value $V_j$ in the Converted Matrix 250 is defined as $V_j = -\ln(V_i)$. In such an embodiment, a value of "one" in the Predictive Matrix 240, which indicates that the patient is known to satisfy the criterion, yields a value of "zero" in the Converted Matrix 250, which indicates that no cost will be incurred to confirm eligibility, with respect to the criterion. Similarly, a value of "zero" in the Predictive Matrix 240, which indicates that the patient is known to fail the criterion, yields a value of "positive infinity" in the Converted Matrix 250, which indicates that no amount of expenditure can be used to confirm eligibility, with respect to the criterion. In an embodiment, the Converted Matrix 250 essentially acts as a cost-multiplier to generate utilized costs.

As illustrated, the Utilization Predictor 125 then makes a Utilization Determination 255 to generate a set of Utilized Cost Predictions 130. In one embodiment, the Utilization Determination 255 is performed by computing the dot product between the Converted Matrix 250 and the Cost Vectors 110. In such an embodiment, the Utilization Predictor 125 determines, for each patient, a predicted utilized cost with respect to each unknown condition. The Utilization Predictor 125 can then aggregate these condition-specific costs (e.g., by summing) in order to determine the total utilized cost (denoted as u1 through u6 in FIG. 2C). In an embodiment, for a given patient and condition, the condition-specific utilized cost is computed by multiplying the corresponding value in the Converted Matrix 250 by the corresponding value in the Cost Vectors 110 (e.g., the total or aggregate cost of evaluating the relevant condition). For example, in order to generate a utilized cost u4 for patient P4, the Utilization Predictor 125 first computes P4's condition-specific utilized cost for Condition1 by multiplying the corresponding value in the Converted Matrix 250 (0.198 in the illustrated example) by the total evaluation cost of Condition1 (c1, as illustrated in FIG. 2A). Once this is repeated for each (unknown) value for the patient P4, the results can be summed to generate the total utilized cost u4.

In an embodiment, the patients can then be ranked, sorted, or filtered based on their utilized costs. In an embodiment, the Utilization Predictor 125 can recommend the patients for evaluation, in order of their utilized costs. Additionally, in one embodiment, if a given patient is selected, the Utilization Predictor 125 can provide the condition-specific costs, such that the healthcare provider or other user can determine the order in which the needed examination(s) should be performed. In this way, resource expenditure is minimized during the evaluation process. Further, the total number of patients to be evaluated is reduced. That is, because the Utilization Predictor 125 intelligently recommends an order of evaluation, the number of patients that will undergo (and fail) evaluation is significantly reduced. This improves the operations of the system, as well as the results of the clinical trial.

Figure 3:
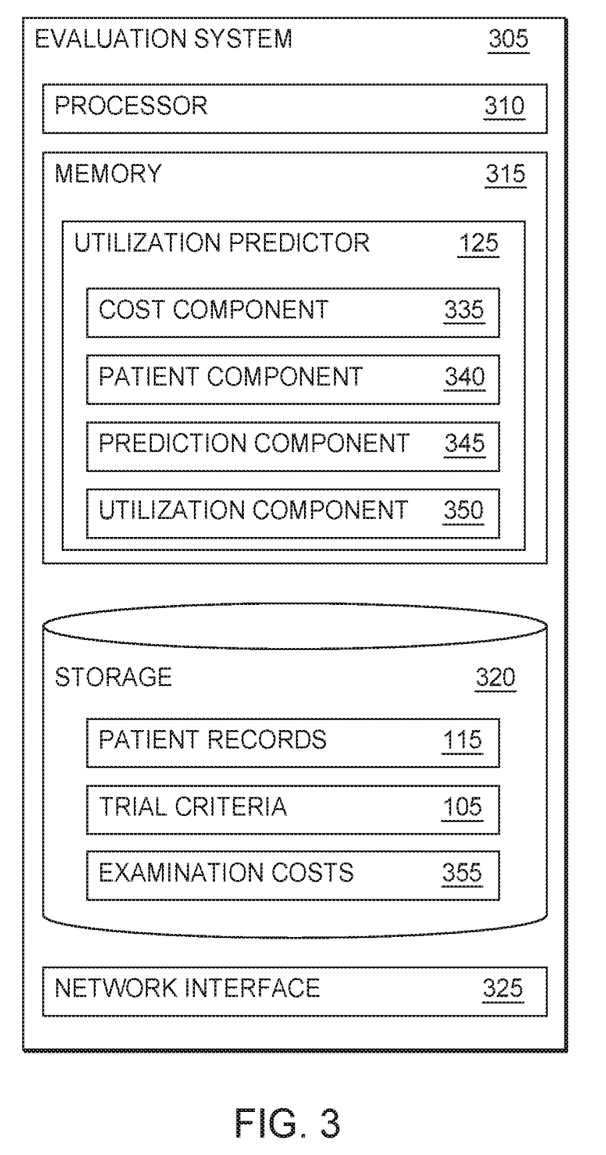
FIG. 3 is a block diagram illustrating an evaluation system configured to predict utilized costs for trial recruitment, according to one embodiment disclosed herein.

FIG. 3 is a block diagram illustrating an Evaluation System 305 configured to predict utilized costs for trial recruitment, according to one embodiment disclosed herein. Although depicted as a physical device, in embodiments, the Evaluation System 305 may be implemented using virtual device(s), and/or across a number of devices (e.g., in a cloud environment). As illustrated, the Evaluation System 305 a Processor 310, Memory 315, Storage 320, and a Network Interface 325. In the illustrated embodiment, the Processor 310 retrieves and executes programming instructions stored in Memory 315, as well as stores and retrieves application data residing in Storage 320. The Processor 310 is generally representative of a single CPU, multiple CPUs, a single CPU having multiple processing cores, and the like. The Memory 315 is generally included to be representative of a random access memory. Storage 320 may be any combination of disk drives, flash-based storage devices, and the like, and may include fixed and/or removable storage devices, such as fixed disk drives, removable memory cards, caches, optical storage, network attached storage (NAS), or storage area networks (SAN). In an embodiment, the Storage 320 is a heterogeneous system of layers, where each layer corresponds to a different type of storage and/or storage with a different cost of access. Via the Network Interface 325, the Evaluation System 305 can be communicatively coupled with one or more other devices and components (e.g., EMR repositories, user terminals, and the like).

In the illustrated embodiment, the Storage 320 includes one or more Patient Records 115, one or more sets of Trial Criteria 105, and one or more indications of Examination Costs 355. Although depicted as residing in Storage 320 for conceptual clarity, in embodiments, the Patient Records 115, Trial Criteria 105, and Examination Costs 355 may reside in any suitable location, including in Memory 315 or in one or more remote repositories. In an embodiment, the Patient Records 115 include EMRs indicating attributes of any number of patients, such as the patients' conditions, disorders, characteristics, statuses, and the like. The Patient Records 115 may include natural language text documents, structured or parsed data, and the like.

In embodiments, the Trial Criteria 105 are inclusion and/or exclusion criteria for any number of clinical trials. In an embodiment, each criterion specifies one or more medical conditions or characteristics (such as age, weight, blood pressure, disease status, and the like), as well as one or more acceptable and/or unacceptable values for each condition. For example, the Trial Criteria 105 may indicate that, for a first study, participants must "be at least 35 years of age," "not have diabetes," and "weigh less than three hundred pounds." In embodiments, the Trial Criteria 105 may include natural language text statements, structured or parsed data (e.g., representing the criteria in machine-readable format), and the like.

In an embodiment, the Examination Costs 355 are predefined costs associated with a variety of examinations, tests, surveys, questionnaires, and the like. Generally, the Examination Costs 355 reflect the cost of determining a patient value for any number of attributes. For example, a first Examination Cost 355 may reflect the cost of determining the size of a patient's tumor, while a second Examination Cost 355 reflects the cost of determining a patient's blood sugar levels. In embodiments, the Examination Costs 355 may include monetary cost, time required to determine a value, an indication of how invasive the examination is for the patient, and the like. In some embodiments, the Examination Costs 355 further include an aggregate numerical value for the overall "cost" of the examination, taking into account each dimension of cost (along with dimension-specific weights, in some embodiments).

In the illustrated embodiment, the Memory 315 includes a Utilization Predictor 125. Although depicted as software residing in Memory 315, in embodiments, the functionality of the Utilization Predictor 125 can be implemented using software, hardware, or a combination of hardware and software. As illustrated, the Utilization Predictor 125 includes a Cost Component 335, a Patient Component 340, a Prediction Component 345, and a Utilization Component 350. Although depicted as discrete components for conceptual clarity, in embodiments, the operations of the Cost Component 335, Patient Component 340, Prediction Component 345, and Utilization Component 350 may be combined or distributed across any number of components.

In an embodiment, the Cost Component 335 constructs Cost Vectors 110 based on the Trial Criteria 105 and Examination Costs 355. In one such embodiment, the Cost Component 335 receives Trial Criteria 105 and, for each criterion, identifies the corresponding Examination Cost(s) 355 (e.g., based on the relevant condition(s)). The Cost Component 335 can then construct Cost Vectors 110 for the Trial Criteria 105, reflecting the potential costs of testing or evaluating each of the Trial Criteria 105. In some embodiments, if the Examination Costs 355 are multi-dimensional, the Cost Component 335 receives (e.g., from a user), a selection of one or more of the dimensions that should be considered, and/or an indication of the weight to be applied to each. Additionally, in on embodiment, the Cost Component 335 can select from multiple tests or examinations. For example, if there are two or more examinations that could be used to resolve a given criterion, the Cost Component 335 can determine which examinations are preferred and/or available (e.g., based on geographic location, cost, user-specification, and the like).

In the illustrated embodiment, the Patient Component 340 retrieves or receives Patient Records 115 and generates the Patient Matrix 120. In one embodiment, generating the Patient Matrix 120 comprises creating a column for each condition specified in the Trial Criteria 105, and a row for each potential participant. The Patient Component 340 can then parse the Patient Records 115 to fill the Patient Matrix 120 with any known values of the patients. In some embodiments, the Patient Matrix 120 additionally includes one or more columns corresponding to conditions or attributes of the patients that are not mentioned in the Trial Criteria 105. In such an embodiment, these additional columns may be useful in generating accurate predictions. In some embodiments, the Patient Component 340 additionally applies the Trial Criteria 105 to create a Binary Matrix 230. In other embodiments, the Prediction Component 345 creates the Binary Matrix 230.

In one embodiment, the Prediction Component 345 applies ML to generate predictive values for each unknown value in the Binary Matric 230, in order to build the Predictive Matrix 240. In some embodiments, the Prediction Component 345 uses matrix factorization to form the Predictive Matrix 240. In one embodiment, the Prediction Component 345 generates predictive values based on similar patients. For example, in one such embodiment, for an index patient, the Prediction Component 345 identifies a set of patients with similar attributes or values in the Binary Matrix 230 and/or Patient Matrix 120 (e.g., based on determining that the cosine similarity between the patients exceeds a threshold). The Prediction Component 345 can then determine, for each unknown value of the index patient, the corresponding value of each similar patient (if known). Based on these values, the Prediction Component 345 can generate a predicted value for the index patient.

In the illustrated embodiment, the Utilization Component 350 receives the Predictive Matrix 240 and the Cost Vectors 110, and generates a set of Utilized Cost Predictions 130. In one embodiment, the Utilization Component 350 first computes the negative natural log of each value in the Predictive Matrix 240. The Utilization Component 350 can then, for each patient, generate the utilized cost with respect to each criterion that is not known to be satisfied or unsatisfied. Additionally, in some embodiments, the Utilization Component 350 generates an overall utilized cost for each patient based on the criterion-specific costs (e.g., by summing them).

Figure 4:
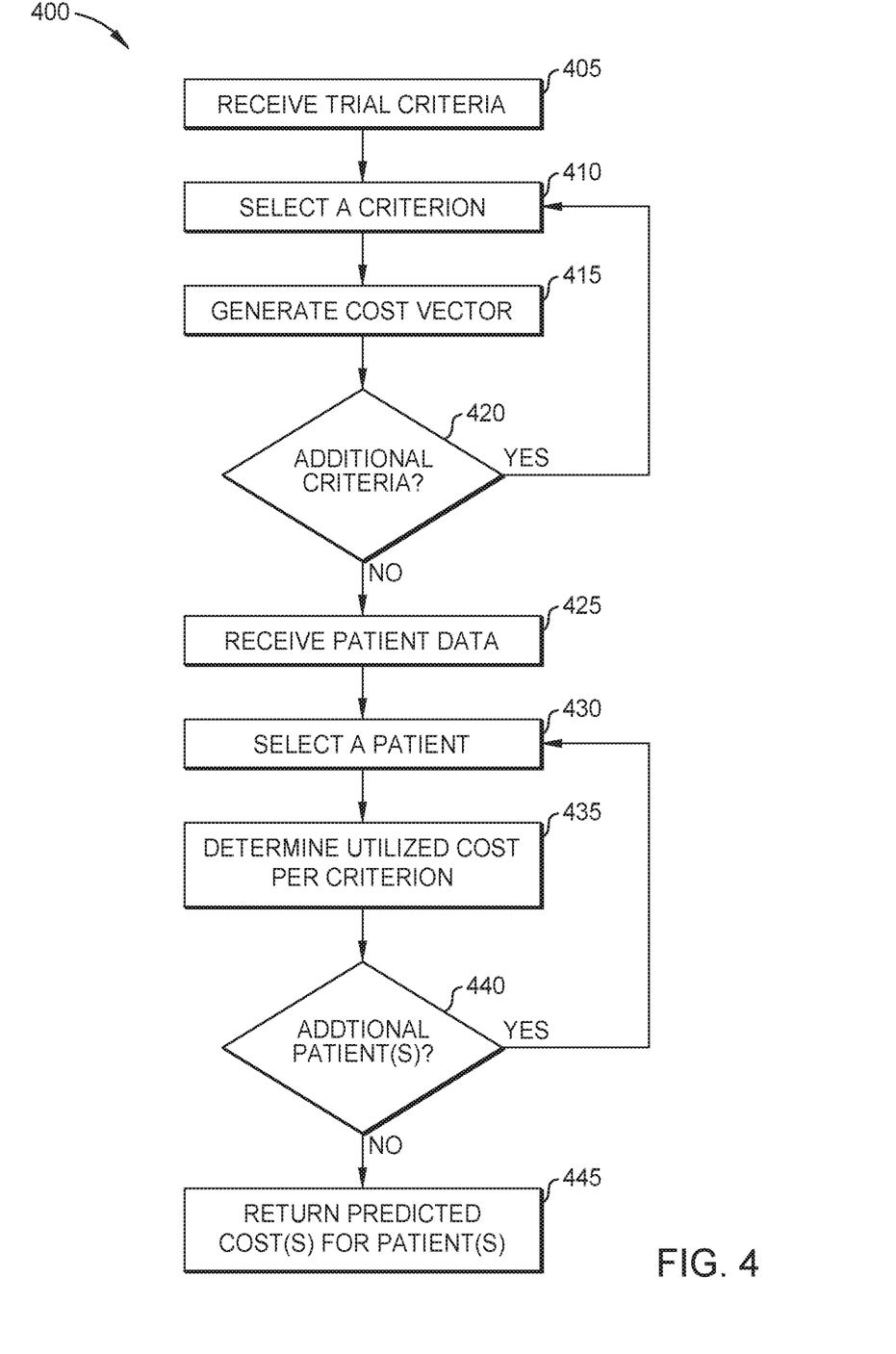
FIG. 4 is a flow diagram illustrating a method of evaluating patient data to generate utilized cost predictions, according to one embodiment disclosed herein.

FIG. 4 is a flow diagram illustrating a method 400 of evaluating patient data to generate utilized cost predictions, according to one embodiment disclosed herein. The method 400 begins at block 405, where the Utilization Predictor 125 receives trial criteria associated with a clinical trial for which a user would like to identify and recruit eligible participants. At block 410, the Utilization Predictor 125 selects one of the criteria used to define eligibility for the trial. As discussed above, in embodiments, each criterion specifies one or more conditions or medical attributes, as well as one or more acceptable values (or ranges) for these conditions or attributes. The method 400 then continues to block 415, where the Utilization Predictor 125 generates a cost vector for the selected criterion. In an embodiment, the Utilization Predictor 125 accesses predefined cost structures (e.g., defined by a user) in order to generate the cost vector. In another embodiment, the Utilization Predictor 125 parses medical literature to generate cost structures.

In one embodiment, the cost vector for a given criterion defines the costs that will be incurred to determine whether a patient with one or more unknown attributes satisfies or fails the criterion. For example, the cost vector can be based in part on the monetary and time costs required to perform one or more diagnostics or examinations that are used to determine value(s) for the relevant conditions. Of course, if the relevant values are already known for a given patient, there will be zero costs incurred to determine eligibility with respect to the selected criterion. In embodiments, the cost vectors define predicted expenditures for each patient who has an unknown status with respect to the relevant condition(s).

The method 400 then proceeds to block 420, where the Utilization Predictor 125 determines whether there is at least one additional criterion that has not yet been analyzed. If so, the method 400 returns to block 410. Otherwise, the method 400 continues to block 425, where the Utilization Predictor 125 receives patient data for one or more patients. In some embodiments, the patient data includes one or more EMRs with natural language text. In at least one embodiment, the patient data includes pre-processed and parsed patient data that is presented in a machine-readable format (e.g., in key-value pairs). At block 430, the Utilization Predictor 125 selects one of the patients reflected in the patient data. The method 400 then continues to block 435.

At block 435, the Utilization Predictor 125 determines a predicted utilized cost on a per-criterion basis, with respect to the selected patient. In one embodiment, to do so, the Utilization Predictor 125 identifies criteria that the selected patient satisfies (based on the patient data), and assigns a utilized cost of 0 to these criteria. Further, in some embodiments, the Utilization Predictor 125 identifies criteria that the selected patient fails, and assigns each an indication of infinite cost or impossible costs. Additionally, in an embodiment, for criteria that cannot be evaluated with respect to the selected patient (e.g., because one or more values or attributes are unknown for the patient), the Utilization Predictor 125 can generate a probability that the patient will satisfy each such criterion, and generate a utilized cost for each based on the corresponding cost vectors. In some embodiments, the Utilization Predictor 125 further aggregates the criterion-specific (or condition-specific) utilized cost predictions to generate an overall patient-specific utilized cost.

At block 440, the Utilization Predictor 125 determines whether there is at least one additional patient to be evaluated. If so, the method 400 returns to block 430. If not, the method 400 continues to block 445. At block 445, the Utilization Predictor 125 returns the predicted costs for each patient. In an embodiment, the predicted cost for a given patient corresponds to the utilized cost expected to show eligibility for the trial. Of course, the actual cost required to determine eligibility may be higher. Similarly, some patients will likely be found ineligible. Nevertheless, the predicted utilized costs can be used to sort and/or filter patients in order to minimize expenditures while identifying eligible participants.

Figure 5:
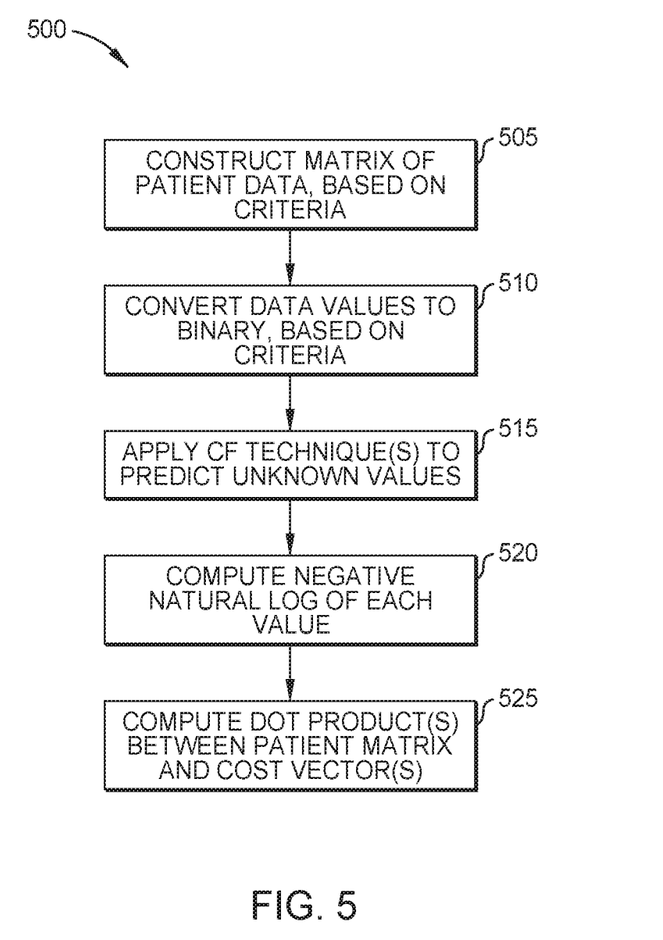
FIG. 5 is a flow diagram illustrating a method of processing patient data to rank individuals and tests, according to one embodiment disclosed herein.

FIG. 5 is a flow diagram illustrating a method 500 of processing patient data to rank individuals and tests, according to one embodiment disclosed herein. The method 500 begins at block 505, where the Utilization Predictor 125 constructs a matrix of patient data (e.g., a Patient Matrix 120) based on received trial criteria and patient records. In one embodiment, the Utilization Predictor 125 does so by creating a matrix with a column for each condition specified in the trial criteria, and adds a row for each patient reflected in the patient records. The method 500 then continues to block 510, where the Utilization Predictor 125 converts the data in the patient matrix to binary values, based on the trial criteria.

In some embodiments, the Utilization Predictor 125 does so by determining, for each known value in the patient matrix, whether the value satisfies the corresponding criterion. If so, the value is converted to a one. If not, the value is converted to a zero. The method 500 then proceeds to block 515, where the Utilization Predictor 125 applies one or more CF techniques (such as matrix factorization) in order to generate predicted values for any empty fields in the matrix (representing unknown values). At block 520, the Utilization Predictor 125 proceeds to compute the negative natural log of each value in the matrix. Finally, at block 525, the Utilization Predictor 125 computes the dot product(s) between the matrix and the cost vectors, as discussed above. This yields utilized cost predictions for each patient-criterion combination. Further, in some embodiments, the criterion-specific costs are aggregated to generate overall utilized costs for each patient.

Figure 6:
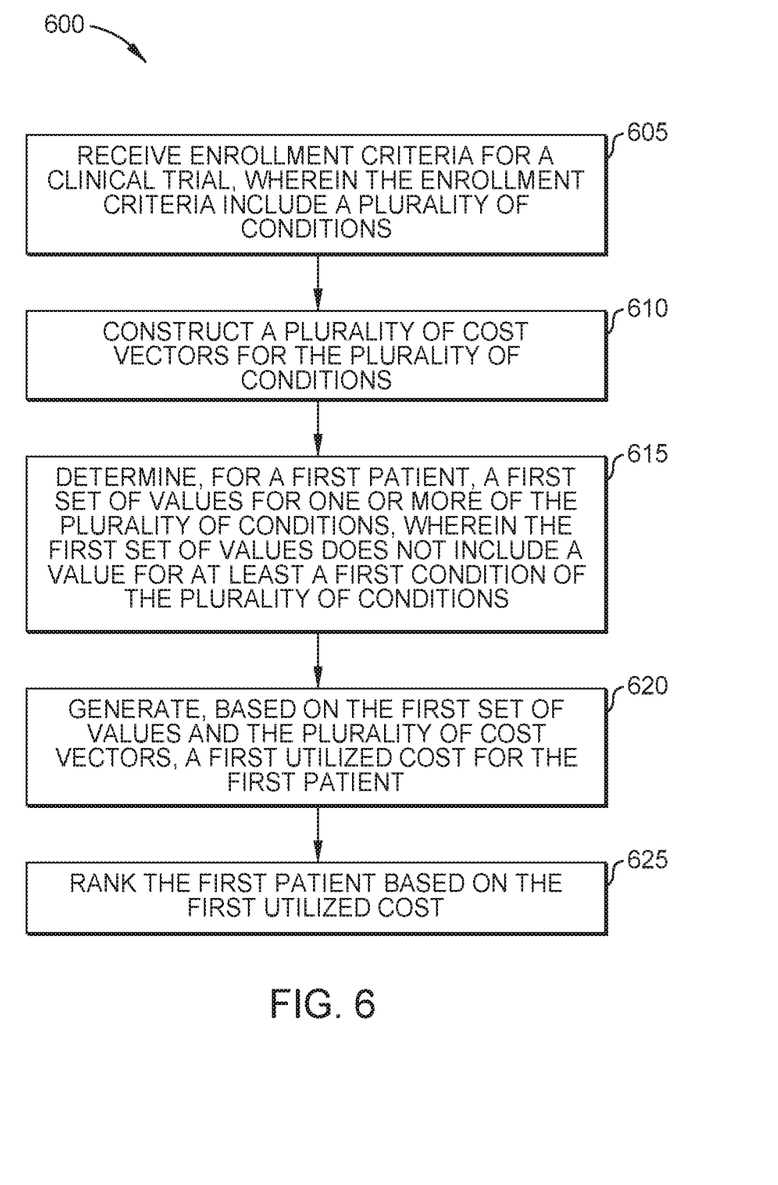
FIG. 6 is a flow diagram illustrating a method of generating utilized cost values, according to one embodiment disclosed herein.

FIG. 6 is a flow diagram illustrating a method 600 of generating utilized cost values, according to one embodiment disclosed herein. The method 600 begins at block 605, where a Utilization Predictor 125 receives enrollment criteria for a clinical trial, wherein the enrollment criteria include a plurality of conditions. At block 610, the Utilization Predictor 125 constructs a plurality of cost vectors for the plurality of conditions. Additionally, at block 615, the Utilization Predictor 125 determines, for a first patient, a first set of values for one or more of the plurality of conditions, wherein the first set of values does not include a value for at least a first condition of the plurality of conditions. The method 600 then proceeds to block 620 where the Utilization Predictor 125 generates, based on the first set of values and the plurality of cost vectors, a first utilized cost for the first patient. At block 625, the Utilization Predictor 125 ranks the first patient based on the first utilized cost.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding and following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding and following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Utilization Predictor 125) or related data available in the cloud. For example, the Utilization Predictor 125 could execute on a computing system in the cloud and evaluate patient data to generate utilized costs. In such a case, the Utilization Predictor 125 could evaluate data and store predicted utilized costs at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
receiving enrollment criteria for a clinical trial, wherein the enrollment criteria include a plurality of conditions;
constructing a plurality of cost vectors for the plurality of conditions;
determining, for a first candidate, a first set of values for one or more of the plurality of conditions, wherein the first set of values does not include a value for at least a first condition of the plurality of conditions;
generating, based on the first set of values and the plurality of cost vectors, a first utilized cost for the first candidate using a machine learning model trained to generate predicted values for the plurality of conditions based on input patient attributes;
ranking the first candidate and at least a second candidate based on the first utilized cost and a second utilized cost for the second candidate;
filtering the second candidate from the ranking based on the second utilized cost;
selecting the first candidate, based on the first utilized cost, to expend additional resources performing clinical tests, wherein the additional resources are not expended for the second candidate;
upon receiving the selection of the first candidate, generating a ranking for a first clinical test for the first candidate, comprising:
identifying other candidates that are similar to the first candidate as determined by known attributes of the first candidate;
generating, for the first candidate, a first probability that the first candidate will have an acceptable value for the first condition, comprising:
determining a probable outcome of the first clinical test, if applied to the first candidate, based on the outcomes of the other candidates, comprising:
generating a candidate matrix, wherein the candidate matrix includes a respective row for each respective candidate, and a respective column for each respective condition of the plurality of conditions; and
performing one or more collaborative filtering (CF) techniques on the candidate matrix; and
identifying a condition that satisfies the enrollment criteria;
determining a probability that the first clinical test will cause the first candidate to be eligible for the clinical trial, based on the first probability; and
determining a cost of the first clinical test; and
performing the first clinical test for the first candidate.

2. The method of claim 1, the method further comprising:
prior to performing the one or more CF techniques on the candidate matrix, converting each respective value in the candidate matrix to a respective binary value based on whether the respective value satisfies the enrollment criteria.

3. The method of claim 1, the method further comprising:
prior to generating the first utilized cost, computing a negative natural log of the first probability.

4. The method of claim 1, the method further comprising:
ranking, based on the first probability and a first cost vector of the plurality of cost vectors, one or more clinical tests for the first candidate, wherein the first cost vector corresponds to the first condition.

5. The method of claim 1, wherein each respective cost vector of the plurality of cost vectors corresponds to a respective condition of the plurality of conditions and indicates a respective cost of a respective clinical test needed to determine a value for the respective condition, with respect to a respective candidate.

6. The method of claim 5, wherein each respective cost vector of the plurality of cost vectors indicates at least one of:
   (i) a monetary cost of performing the respective clinical test;
   (ii) a time required to perform the respective clinical test; and
   (iii) an invasiveness of performing the respective clinical test.

7. A computer-readable storage medium containing computer program code that, when executed by operation of one or more computer processors, performs an operation comprising:
   receiving enrollment criteria for a clinical trial, wherein the enrollment criteria include a plurality of conditions;
   constructing a plurality of cost vectors for the plurality of conditions;
   determining, for a first candidate, a first set of values for one or more of the plurality of conditions, wherein the first set of values does not include a value for at least a first condition of the plurality of conditions;
   generating, based on the first set of values and the plurality of cost vectors, a first utilized cost for the first candidate using a machine learning model trained to generate predicted values for the plurality of conditions based on input patient attributes;
   ranking the first candidate and at least a second candidate based on the first utilized cost and a second utilized cost for the second candidate;
   filtering the second candidate from the ranking based on the second utilized cost;
   selecting the first candidate, based on the first utilized cost, to expend additional resources performing clinical tests, wherein the additional resources are not expended for the second candidate;
   upon receiving the selection of the first candidate, generating a ranking for a first clinical test for the first candidate, comprising:
      identifying other candidates that are similar to the first candidate as determined by known attributes of the first candidate;
      generating, for the first candidate, a first probability that the first candidate will have an acceptable value for the first condition, comprising:
         determining a probable outcome of the first clinical test, if applied to the first candidate, based on the outcomes of the other candidates, comprising:
            generating a candidate matrix, wherein the candidate matrix includes a respective row for each respective candidate, and a respective column for each respective condition of the plurality of conditions; and
            performing one or more collaborative filtering (CF) techniques on the candidate matrix; and
         identifying a condition that satisfies the enrollment criteria;
         determining a probability that the first clinical test will cause the first candidate to be eligible for the clinical trial, based on the first probability; and
         determining a cost of the first clinical test; and
      performing the first clinical test for the first candidate.

8. The computer-readable storage medium of claim 7, the operation further comprising:
   prior to performing the one or more CF techniques on the candidate matrix, converting each respective value in the candidate matrix to a respective binary value based on whether the respective value satisfies the enrollment criteria.

9. The computer-readable storage medium of claim 7, the operation further comprising:
   prior to generating the first utilized cost, computing a negative natural log of the first probability.

10. The computer-readable storage medium of claim 7, the operation further comprising:
    ranking, based on the first probability and a first cost vector of the plurality of cost vectors, one or more clinical tests for the first candidate, wherein the first cost vector corresponds to the first condition.

11. A system comprising:
    one or more computer processors; and
    a memory containing a program which when executed by the one or more computer processors performs an operation, the operation comprising:
       receiving enrollment criteria for a clinical trial, wherein the enrollment criteria include a plurality of conditions;
       constructing a plurality of cost vectors for the plurality of conditions;
       determining, for a first candidate, a first set of values for one or more of the plurality of conditions, wherein the first set of values does not include a value for at least a first condition of the plurality of conditions;
       generating, based on the first set of values and the plurality of cost vectors, a first utilized cost for the first candidate using a machine learning model trained to generate predicted values for the plurality of conditions based on input patient attributes;
       ranking the first candidate and at least a second candidate based on the first utilized cost and a second utilized cost for the second candidate;
    filtering the second candidate from the ranking based on the second utilized cost;
       selecting the first candidate, based on the first utilized cost, to expend additional resources performing clinical tests, wherein the additional resources are not expended for the second candidate;
       upon receiving the selection of the first candidate, generating a ranking for a first clinical test for the first candidate, comprising:
          identifying other candidates that are similar to the first candidate as determined by known attributes of the first candidate;
          generating, for the first candidate, a first probability that the first candidate will have an acceptable value for the first condition, comprising:
             determining a probable outcome of the first clinical test, if applied to the first candidate, based on the outcomes of the other candidates, comprising:
                generating a candidate matrix, wherein the candidate matrix includes a respective row for each respective candidate, and a respective column for each respective condition of the plurality of conditions; and performing one or more collaborative filtering (CF) techniques on the candidate matrix; and identifying a condition that satisfies the enrollment criteria;

determining a probability that the first clinical test will cause the first candidate to be eligible for the clinical trial, based on the first probability; and determining a cost of the first clinical test; and performing the first clinical test for the first candidate.

12. The system of claim 11, the operation further comprising:

prior to performing the one or more CF techniques on the candidate matrix, converting each respective value in the candidate matrix to a respective binary value based on whether the respective value satisfies the enrollment criteria.

13. The system of claim 11, the operation further comprising:

prior to generating the first utilized cost, computing a negative natural log of the first probability.

14. The system of claim 11, the operation further comprising:

ranking, based on the first probability and a first cost vector of the plurality of cost vectors, one or more clinical tests for the first candidate, wherein the first cost vector corresponds to the first condition.

* * * * *